(12) United States Patent
Tajima

(10) Patent No.: US 7,369,241 B2
(45) Date of Patent: May 6, 2008

(54) CONTINUOUS OPTICAL MEASURING APPARATUS AND CONTINUOUS OPTICAL MEASURING METHOD

(75) Inventor: Hideji Tajima, Matsudo (JP)

(73) Assignee: Universal Bio Research Co., Ltd., Matsudo-Shi, Chiba (JP)

( * ) Notice: Subject to any disclaimer, the term of this patent is extended or adjusted under 35 U.S.C. 154(b) by 170 days.

(21) Appl. No.: 10/543,471

(22) PCT Filed: Feb. 2, 2004

(86) PCT No.: PCT/JP2004/001001

§ 371 (c)(1),
(2), (4) Date: May 9, 2006

(87) PCT Pub. No.: WO2004/068125

PCT Pub. Date: Aug. 12, 2004

(65) Prior Publication Data

US 2006/0268276 A1    Nov. 30, 2006

(30) Foreign Application Priority Data

Jan. 31, 2003   (JP) ............................. 2003-025290

(51) Int. Cl.
*G01N 21/00*   (2006.01)
(52) U.S. Cl. ...................... 356/432; 356/440
(58) Field of Classification Search ........ 356/432–444, 356/246, 336–339, 36–42
See application file for complete search history.

(56) References Cited

U.S. PATENT DOCUMENTS 5,045,703 A * 9/1991 Wieboldt et al. ........... 250/352
2003/0064836 A1   4/2003 Moss et al.

FOREIGN PATENT DOCUMENTS

| JP | 11-94747 | 4/1999 |
|---|---|---|
| JP | 2001-238674 | 9/2001 |
| WO | WO 01/53831 | 7/2001 |

OTHER PUBLICATIONS

Japanese Patent Office, "International Search Report," International Application No. PCT/JP2004/001001, Apr. 6, 2004, 2 pages.

* cited by examiner

*Primary Examiner*—Gregory J. Toatley, Jr.
*Assistant Examiner*—Tri Ton
(74) *Attorney, Agent, or Firm*—Haynes and Boone, LLP

(57) ABSTRACT

An inexpensive continuous optical measuring apparatus with high cost/performance ratio capable of obtaining the emission of light at respective fixed positions arranged on a foundation member, by a simple device or a control, and a continuous optical measuring method. The apparatus includes at least one transparent or semi-translucent storage part capable of storing the foundation member having a plurality of types of predetermined detection substances fixed thereto along an arrangement line at predetermined intervals, with the detection substances and their fixed positions associated; at least one light receiving part installed at a predetermined position outside of the storage part.

16 Claims, 5 Drawing Sheets

CONTINUOUS OPTICAL MEASURING APPARATUS AND CONTINUOUS OPTICAL MEASURING METHOD

CROSS REFERENCE

This application is a United States national phase application of co-pending international patent application number PCT/JP2004/001001, filed Feb. 2, 2004, which claims priority to Japanese patent application number 2003-25290, filed Jan. 31, 2003 which priority is claimed.

TECHNICAL FIELD

The present invention relates to a continuous optical measuring apparatus and a continuous optical measuring method. The present invention relates to various fields requiring treatment of biopolymers or biological low molecular substances such as genes, substances of immune systems, amino acids, proteins, sugars, and the like, for example engineering fields, agricultural fields such as food processing, agricultural processing, and fishery processing, pharmaceutical fields, medical fields such as sanitation, health, immunization, diseases, and genetics, and chemical fields, and the like.

In particular, the present invention relates to a continuous optical measuring apparatus and a continuous optical measuring method which are suitable for gene mutation analysis, polymorphism analysis, mapping, base sequence analysis, expression analysis, and the like.

BACKGROUND ART

Conventionally, there have been inventions where a DNA chip is used for determining the gene base sequence (U.S. Pat. No. 5,445,934 and U.S. Pat. No. 5,744,305).

The DNA chip is a plate such as a semiconductor film or a slide glass on which many types of known oligonucleotides are arranged in an array form and fixed to the surface thereof such that the respective minute amounts of suspensions are in dot form. The DNA chip is manufactured such that, in order to form an array of a large number of oligonucleotides on its narrow surface, minute amounts of oligonucleotide suspensions are dispensed at predetermined intervals one by one using a pipette device while avoiding contamination. Various genetic assays and analysis are performed using the DNA chip.

For example, in order to determine an unknown base sequence of a target gene, conventionally, a user dispenses a solution suspended with a target gene substance which is labeled with a luminescent substance, onto the DNA chip. After a predetermined reaction time, excess suspension is removed by washing. Next, by detecting the light emission from the DNA chip, the base sequence is determined from the position where the light emission is detected.

Incidentally, in order to manufacture the DNA chip, if an attempt is made to arrange as many types of oligonucleotides as possible in a narrow area with a high density in a planar form, they come close to each other. As a result, not only is cross contamination easily generated, but also the amounts of the oligonucleotides are further decreased at the respective fixed positions. In particular, if the amounts of the oligonucleotides are decreased at the respective fixed positions, errors easily occur in the determination of the light emitting positions, and there are problems in accuracy.

Moreover, conventionally, there has been used a DNA chip wherein substances such as respective oligonucleotides are fixed on a plane surface such as a glass plate in the form of a prepared slide having a size of about 2.6 cm×7.6 cm. In order to supply a liquid to substances such as the oligonucleotides at the respective fixed positions on the plane surface, a method has been taken wherein, after dispensing about 10 µl of liquid only on the plane surface, a glass plate or a film is manually mounted on the plane surface in a sandwich form, so that a uniform thin liquid layer is formed, and a minute amount of liquid is evenly supplied to the respective fixed positions. In this method, the step for mounting the film or the like has been an obstacle against work automation. Moreover, since the liquid is supplied by mounting the film or the like, it is difficult to fluidize the liquid to be supplied. Furthermore, due to the decrease in the amount, the encountability and the reactivity with the target substance is further decreased, causing a problem in that the process takes time, and a highly dense liquid is required for the process.

Moreover, since the sample is disposed in a planar form, the treatment and the automation become more difficult as the density is increased. Consequently, a very large amount of time and labor is required to manufacture the DNA chip, which increases the price. In particular, in order to analyze, assay, and determine an unknown target substance including a huge amount of base sequences, a large amount of DNA chips are required to be analyzed, assayed, and the like. Therefore, the inventor of the present application has made an invention to solve the problem (International Publication No. WO 01/53831, International Publication No. WO 01/61361, and International Publication No. WO 01/69249), and has disclosed an integrated support having: at least one foundation member formed in a slender shape such as a thread, a cord, a tape, or a rod; and various detection substances fixed in lines in the longitudinal direction of the foundation member having predetermined chemical structures, wherein the foundation member is rolled, laminated, or aligned, and the fixed positions of the various detection substances and the respective chemical structures thereof are associated.

Furthermore, heretofore, as performed by the inventor of the present application, in order to examine the bond of the respective fixed positions and a target substance tagged with a labeling substance, the overall fixed positions or a plurality of fixed positions are measured at once, and the light emission at the respective fixed positions is measured, so as to efficiently examine the chemical structure of the target substance and the affinity thereof (International Publication No. WO 02/063300).

However, even if the manufacture of such an integrated support is easy and the cost is low, there has been a problem in that the advantage of the integrated support is not sufficiently demonstrated unless the reaction, the measurement, and the identification using the integrated support can be efficiently and quickly performed.

On the other hand, if the DNA chip is optically measured, since the DNA chip is a two-dimensional array on a plane surface, in order to measure the light emission at the respective fixed positions, it is necessary to move the light receiving part along a complicated route where the direction and the position are discontinuously changed for the measurement, for example, so as to move it in the Y axis direction while reciprocating along the X axis direction. Therefore, there has been a problem in that the apparatus may be complicated and the scale of the apparatus enlarged.

Moreover, as in the conventional manner, if the presence/absence of a target substance tagged with one type of labeling substance is mainly detected, then regarding a large number of labeled fixed positions, the presence/absence of the labeling substance at the respective fixed positions can be readily identified even if a plurality of fixed positions are measured at once.

However, recently, it is further required to label many types of target substances for determining and analyzing the DNA base sequence. In order to label many types of target substances in this manner, it is not sufficient to merely use a plurality of different types of labeling substances for the respective fixed positions, but it is necessary to specify the quantity ratio (mass ratio) for the labeling (International Publication No. WO 00/5357). At this time, in order to obtain the information from the labeling substances for the respective fixed positions, it has been necessary to obtain detailed information on the respective fixed positions.

Therefore, the present invention has been devised to solve the above problems, with a first object of providing an inexpensive continuous optical measuring apparatus with high cost/performance ratio capable of obtaining the emission of light at respective fixed positions arranged on a foundation member, by a simple device or a control, and a continuous optical measuring method.

A second object is to provide a reliable continuous optical measuring apparatus capable of obtaining the information on the respective fixed positions arranged on the foundation member accurately and precisely, and a continuous optical measuring method.

A third object is to provide a continuous optical measuring apparatus capable of reliably performing the identification in the labeling performed by changing the quantity ratio of a plurality of types of labeling substances generated as a result of reactions at the respective fixed positions on the foundation member, and a continuous optical measuring method.

A fourth object is to provide a continuous optical measuring apparatus capable of consistently and automatically performing the reaction on the foundation member, the measurement, and the identification of the detection substances or the binding substances, and a continuous optical measuring method A fifth object is to provide a continuous optical measuring apparatus capable of efficiently measuring the light emission at the fixed positions on the foundation member, and a continuous optical measuring method.

DISCLOSURE OF THE INVENTION

In order to solve the above technical problems, a first aspect of the present invention is a continuous optical measuring apparatus comprising: at least one transparent or semi-translucent storage part capable of storing a foundation member having a plurality of types of predetermined detection substances fixed thereto along an arrangement line at predetermined intervals, with the detection substances and their fixed positions associated; at least one light receiving part installed at a predetermined position outside of the storage part, and receiving light from the fixed positions, and receiving light from an area having a light receiving width narrower than the width of the arrangement line; and a continuous moving part which is continuously moved relatively between the light receiving part and the storage part so as to scan the fixed positions on the foundation member along a spiral moving line having the light receiving width.

Here, the "plurality of types of detection substances" mean chemical substances having predetermined chemical structures which can be recognized and bound by specific binding substances including for example, biopolymers or low molecular substances such as nucleic acids, proteins, amino acids, sugar chains, peptides, and the like. The nucleic acids include a double strand DNA, a single strand DNA, cDNA, RNA, an oligonucleotide, a nucleotide, and the like. The binding substances mean chemical substances having a predetermined chemical structure which has bondability with the detection substances, including for example, biopolymers or biological low molecular substances such as nucleic acids, proteins, sugar chains, peptides, and the like. The detecting substance or the binding substance may be a natural molecule or an artificial molecule.

In the present invention, the contacting surface characteristic of the detecting substance and the binding substance having bondability with the detecting substance is mutually complementary. It is used for determination of the structure of the target substance, various assays, or analysis thereof. For example, there are genetic substances such as oligonucleotides, and immunity substances. The genetic substances include nucleic acids (polynucleotides), oligonucleotides of the decomposition product thereof, nucleotides, and the like.

The "predetermined chemical structure" means the molecular structure. For example this is the base sequence in the case of the detecting substance, or the binding substance outer electric substances. Here, "foundation member" is formed from a flexible material or a non-flexible material. That is, the foundation member is not necessarily flexible even if it is in a slender shape such as a thread, a cord, or the like, but it may be a non-flexible material such as a wire or a rod. Moreover, it may be a non-flexible foundation member formed in a coil shape. The material may be for example, an organic material such as a polyethylene, a polystyrene, a polypropylene, a urethane, or the like, an inorganic material such as a glass fiber, a ceramics, a metal, or the like, the combination of organic materials and inorganic materials such as an organic film or tape spread with fine ceramics particles thereon, or the like. The organic material includes not only artificial materials but also natural materials such as a silk, cotton, and the like. Moreover, the foundation member is preferably formed from various porous materials, foam materials, fibrous materials, and corrugated materials, at least at the respective fixed positions.

Here, the foundation member is not necessarily in a slender shape. Moreover, it may be a slender foundation member which is wrapped around a support having various shapes, such as an integrated support. Furthermore, the foundation member may be a three-dimensional figure such as a rotation body, a plate, a column, a prism, and the like. "Fixed (at predetermined intervals)" means the state where, for example if the foundation member is in a slender shape, they are disposed along the longitudinal direction of the foundation member so that the respective fixed positions are measurable from the outside. If the foundation member is in a plate shape, the state is to dispose the substances in a matrix form for example.

The "predetermined interval" means a distance which exceeds spreading, in a case of an assay or an analysis requiring to avoid contact between the adjacent detection substances, considering the fixed amount of the respective detection substances and the spreading thereof. In a case of an assay or an analysis not requiring to avoid contact between the adjacent detection substances, it may be a distance such that the spreading is overlapped. Moreover, the interval is not necessarily constant, and may be other regular or irregular intervals.

Here, the "arrangement line" means a straight or curved line along which the fixed positions are disposed. The width is set so as to cover the respective fixed positions. The arrangement line is a line linking the respective fixed positions so as to cover all fixed positions. If the respective fixed positions are disposed along the wrapped slender foundation member, the arrangement line can be said to be a spiral form along the foundation member. However, the arrangement line is not always necessarily a spiral form having a fixed angle of inclination. For example, if the fixed positions are disposed in a matrix form on a foundation member in a cylindrical shape, prismatic shape, a plate shape, or the like, the arrangement line can be set so as to link the respective fixed positions. The reason for "receiving light from an area having a light receiving width narrower than the arrangement line width" is for measuring the respective fixed positions on the arrangement line in detail. As a result, all areas at the fixed positions can be captured even if light is not emitted. The light receiving width means for example, the diameter of an optical fiber to be used, or the diameter which is reduced or enlarged by a lens system.

The "spiral moving line having the light receiving width" means a spiral having a size such that the line width is the same as the light receiving width, and different from the arrangement line. If the pitch of the moving line is made narrower, light can be received while the same fixed positions are overlapped. Moreover, light can be received only from a part of the respective fixed positions by widely spacing between pitches or adjacent lines. Furthermore, they may be moved while touching between the adjacent light receiving widths or allowing them to overlap each other. Different from with the arrangement line, the same fixed positions can be passed through twice or more.

The "continuous movement" means to move smoothly along the line without stopping, skipping, returning, or rapid or non-continuous turnabout or movement. Consequently, this can be realized by a simple device and control. The movement is a combination of rotational movement and straight line movement.

The "light receiving part" is not necessarily one, but a plural number thereof may be provided corresponding to the respective storage parts. In that case, for example the receiving wavelengths are changed for the respective light receiving parts. The "so as to scan the fixed positions on the foundation member" means to move to cover all fixed positions on the foundation member.

According to the first aspect of the present invention, since along the moving line the light emission at the respective fixed positions along the arrangement line can be measured in detail and while being overlapped, precise and detailed information can be obtained for the respective fixed positions.

Consequently, the labeling at the fixed positions can be reliably captured. In particular, if a plurality of types of labeling substances are combined to change the quantity ratio so as to perform many types of labeling, the data analysis can be made easy, or can be automized.

Moreover, since the rotational movement and the straight line movement can be continually performed for measurement, the device and the control can be simplified and the cost can be reduced.

A second aspect of the present invention is a continuous optical measuring apparatus having a light emitting position judging part which associates light received by the light receiving part with the fixed positions, based on respective intervals between the fixed positions disposed on the arrangement line, the shape and the order of the respective fixed positions, the shape of the arrangement line, or the shape of the moving line.

Here, a mark (luminescent substance, hue, and the like) provided at constant periods may be used for the foundation member so as to facilitate association. The mark may be constituted so as to show the standard intensity of the emission intensity. The "shape of the line" includes numerical values specifying shapes such as the diameter, the pitch, the line width, the light receiving width, and the like.

According to the second aspect of the present invention, since the association can be automatically, readily, and reliably performed based on the intervals between the fixed positions disposed on the arrangement line, the order of the respective fixed positions, and the like, the reliability is high.

A third aspect of the present invention is a continuous optical measuring apparatus having a light emission contents judging part which judges one or more wavelengths or one or more wavelength ranges included in the light received by the light receiving part, and/or their corresponding respective intensities.

According to the present invention, since only the individual light emission from the respective fixed positions is received, a large number of labeling can be performed not only by changing the type or amount of the labeling substance, but also by changing the quantity ratio of a plurality of types of labeling substances, at the respective fixed positions.

The light emission contents judging part uses filters through which only predetermined wavelengths or wavelength ranges can pass, and various photometers which measure the quantity of light passing through the filter.

According to the third aspect of the present invention, the identification can be readily and automatically performed, even if the labeling is performed not only using one type of labeling substance, but also using a plurality of labeling substances while changing the quantity ratio.

A fourth aspect of the present invention is a continuous optical measuring apparatus wherein the continuous moving part has a rotation elevating/lowering part which can rotate the storage part about a predetermined axis of rotation, and linearly move the storage part along the axis of rotation.

In this case, the "storage part", the "foundation member", or the "integrated foundation member" are not necessarily a rotation body, but are preferably a rotation body.

According to the fourth aspect of the present invention, the measurement is performed along the line by the rotation of the storage part about the axis of rotation, and the straight line movement of the storage part along the axis of rotation. Therefore, in particular, if the storage part, the foundation member, or the integrated foundation member are a rotation body, and the line runs along in a spiral form, easy and accurate movement can be performed along the line. Moreover, since the movement is performed only by rotational movement and straight line movement, the structure of the moving mechanism can be simplified.

A fifth aspect of the present invention is a continuous optical measuring apparatus wherein the foundation member is a foundation member in a slender shape such as a thread, a cord, or a tape having the respective fixed positions arranged along the longitudinal direction, and the foundation member is wrapped, laminated or aligned, and integrated in a condition where the respective fixed positions are measurable from the outside. Consequently, the arrangement line corresponds to the wrapped foundation member.

Here, in the present invention the foundation member is, "integrated in a condition where the respective fixed positions are measurable from the outside". For the above purpose, the foundation member is constituted so that it can be measured as a three-dimensional figure, for example. As a result, the measurable area of the detecting substance can be increased and measurement from the outside can be reliably performed, thus increasing reliability. For example, if the foundation member is opaque or semi-translucent, the integration is performed by fixing so as to surround the periphery in the circumferential direction along the vertical direction to the longitudinal direction of the foundation member, so that not only the outermost surface of the foundation member, but also the side surface of the foundation member become measurable, and by wrapping with spacing between the foundation members. As a result, even if the foundation member is wrapped while being distorted, the fixed positions can be measured from the outside. Moreover, it is preferable to fix to a transparent or semi-translucent foundation member. Furthermore, the light receiving parts may be provided at two different positions to receive light in the different directions, so that the respective fixed positions can be measured three-dimensionally by stereoscopic vision. Preferably the foundation member is normally wrapped into only one layer. However, if a transparent or semi-translucent foundation member is measured by stereoscopic vision, it can be wrapped into a plurality of layers.

The integrated support integrated with the foundation member may be provided with a support to be wrapped with the foundation member. As a result, if the foundation member is a flexible material, positioning can be readily and reliably performed. However, if the foundation member is a non-flexible material, the support is not necessarily required.

The "integrated foundation member" is preferably provided with a support, and supported by bundling the respective ends of the foundation member while being pinched into a gap provided in the support and fixed by frictional force.

Furthermore, the integrated support preferably has a structure wherein a gap is formed so that a liquid can smoothly pass between the integrated support and the inner wall of a storage part described later, when the liquid is stored in the storage part. As a result, when the liquid is sucked, the liquid can be reliably in contact with the detection substances or the binding substances. When the liquid is discharged, the liquid can smoothly pass between the integrated support and the inner wall without a residue.

Moreover, when the integrated support or the foundation member is stored in the storage part, it is necessary to fix the position of the integrated support and the foundation member in the storage part to avoid their movement in the storage part due to movement of the storage part.

In such a structure, for example the integrated support is provided with a support (for example, in cylindrical shape or prismatic shape) on which the foundation member is wrapped. It is preferable to realize the structure by providing the support with a protector which prevents contact of the foundation member with the inner wall of the container (including a storage part described later) storing the integrated support. The protector is preferably a support (for example, in cylindrical shape, prismatic shape, or the like) of which the appropriate parts (for example, opposite edges, opposite ends, or the like) are provided with projecting portions projecting from the surface of the support (for example, radially), having a height exceeding the thickness of the wrapped foundation member, and with points which contact with container inner wall.

Moreover, the point of contact of the protector with container inner wall is preferably formed to have as small an area as possible. This is because the amount of remaining liquid might be increased if the area of the point of contact is large. The protector is formed in a shape so as not to obstruct the flow of the fluid in the storage part due to the presence of the protector. For example, this can be avoided by providing notches on a projecting portion formed in a ring shape, or providing pin-shaped projecting portions. By means of this protector, positioning of the integrated support in the storage part can also be performed.

If a minute amount of liquid is handled, the support is preferably formed in a hollow shape. Moreover, the distance from the foundation member to the inner wall of the container is preferably as short as possible. On the other hand, if a relatively large amount of liquid is handled, the support is preferably formed from a hollow and/or porous material.

Furthermore, corrugations, spiral grooves or stripes may be provided on the surface of the support to be wrapped with the foundation member, so that a fluid can readily circulate by making a gap between the foundation members, or providing a gap between the support and the foundation member, by wrapping the foundation member along the corrugations, the grooves or the stripes, or crossing over the corrugations, the grooves or the stripes.

According to the present invention, since the foundation member is wrapped in a condition where the respective fixed positions thereof are measurable from the outside, the labeling of the tagged fixed positions can be readily and reliably detected or measured from the outside. Consequently, if the integrated support is used, the handling is easy not only when performing reaction, but also for measurement, and consistent processing can be performed.

According to the fifth aspect of the present invention, since the foundation member is in a slender shape, the fixed positions can be reliably associated with the detection substances or the binding substances by moving the light receiving part so as to scan all fixed positions along the foundation member.

A sixth aspect of the present invention is a continuous optical measuring apparatus wherein the foundation member or the integrated foundation member, and the storage part are rotation bodies, and are stored so that their central axes coincide. As a result, light can be reliably and clearly received by the light receiving part.

According to the sixth aspect of the present invention, the storage part, foundation member and the like are formed as a rotation body, and stored so that their central axes coincide. Therefore, by combining the rotational movement and straight line movement at a fixed rate, the light receiving part can be readily moved so as to scan the respective fixed positions along the line.

A seventh aspect of the present invention is a continuous optical measuring apparatus wherein the light receiving part in the optical measuring part is provided with an optical system which enables focusing on the respective fixed positions of the foundation member stored in the storage part.

According to the seventh aspect of the present invention, since the light receiving part can reliably focus on the respective fixed positions, the light from the respective fixed positions can be clearly measured.

An eighth aspect of the present invention is a continuous optical measuring apparatus wherein the light receiving part in the optical measuring part is attached with a point of one optical fiber.

According to the eighth aspect of the present invention, since the measurement can be performed by one optical fiber, the structure of the apparatus can be simplified, and hence the cost can be reduced.

In a ninth aspect of the present invention the storage part has a fluid inlet/outlet port, and is detachably attached to a nozzle which communicates with a pressure regulating part which regulates the pressure in the storage part so as to suck and discharge the fluid with respect to the storage part, and the continuous moving part is a nozzle rotation elevating/lowering part that rotates the nozzle about the axis of rotation and elevates/lowers it along the axial direction.

Since the storage part has a fluid inlet/outlet port, the storage part can store not only the foundation member but also a fluid. As a result, reaction of the detection substances of the foundation member with the binding substances contained in the liquid is possible in the storage part. The storage part has a storage opening for storing the foundation member. The storage opening may be used for connecting to a sucking and discharging part, for example.

Moreover, based on the shape or the size of foundation member (or integrated support), the storage part may be formed so that the shape or the size thereof is close to the shape or the size of foundation member (or integrated support), so as to form a narrow gap between the inner wall of the storage part and the foundation member, to enable correspondence with a minute amount.

It is preferable to further provide a moving part which can be relatively moved between the inlet/outlet port and the process area on which outside containers are mounted. As a result, by moving the foundation member while the foundation member is stored in the storage part, the process can be automized and consistently performed.

Moreover, since the storage part in contact with the liquid or the foundation member is detachably attached, cross contamination can be reliably prevented by replacing the whole storage part. Furthermore, by providing a magnetic device outside of the storage part, or by replacing with pipette tips provided with a magnetic device which can separate magnetic particles by attracting them onto the inner wall, it can also serve as a device for handling the magnetic particles, and hence many types of processes can be more efficiently and consistently performed.

According to the ninth aspect of the present invention, while storing the foundation member in the storage part, sucking or discharging of the liquid such as necessary reagent with respect to the storage part, can be performed with respect to the same or different liquids, so that the reaction and washing are performed, in which state the measurement can be performed. Consequently, processes such as reaction, measurement, or the like can be efficiently and consistently performed by a quick and simple operation. Moreover, since various processes can be performed while storing in the storage part, cross contamination can be prevented, and reliability is high. Furthermore, the shape or the size of the storage part is determined based on the shape or the size of the foundation member, and hence the processes can be performed even with a minute amount of liquid.

Furthermore, since the nozzle rotation elevating/lowering part can be used as the continuous passing/moving part of the storage part, the structure of the optical measurement apparatus can be simplified, and the scale of the apparatus as a whole can be controlled.

A tenth aspect of the present invention is a continuous optical measuring apparatus having a holding part which rotatably holds a lower part of the storage part so that the storage part can be positioned at a position allowing the light receiving part to receive light.

According to the tenth aspect of the present invention, by rotatably holding the lower part of the storage part, reliable positioning can be performed.

An eleventh aspect of the present invention is a continuous optical measuring apparatus wherein the light receiving part is supported so that minute movements can be made so as to keep the distance from the storage part constant, in accordance with fluctuations accompanying the rotational movement of the storage part.

According to the eleventh aspect of the present invention, even if the shaft center is displaced or fluctuated due to the distortion of the product itself accompanying the rotational movement of the storage part, the distance from the light receiving part to the respective fixed positions can be maintained constant, and hence reliable measurement can be performed.

A twelfth aspect of the present invention is a continuous optical measuring apparatus wherein the optical fiber can irradiate predetermined light through the optical fiber, and can receive light through the optical fiber.

According to the twelfth aspect of the present invention, if the binding substances are labeled with fluorescent substances and the like, excitation light can be irradiated using the optical fiber which receives the light. Consequently, the structure of the apparatus can be simplified.

A thirteenth aspect of the present invention is a continuous optical measuring method comprising: a storing step for storing into at least one transparent or semi-translucent storage part a foundation member having a plurality of types of predetermined detection substances fixed thereto along an arrangement line at predetermined intervals, with the detection substances and their fixed positions associated; a moving step for moving so as to position at least one light receiving part which receives light from an area having a light receiving width narrower than the width of the arrangement line, from the storage part, to a predetermined position outside of the storage part; and a continuous measuring step for measuring while continuously moving relatively between the light receiving part and the storage part so as to scan the fixed positions on the foundation member along a spiral moving line having the light receiving width.

In the thirteenth aspect of the present invention, as described in the first aspect of the present invention, since along the moving line the light emission at the respective fixed positions along the arrangement line can be measured in detail while being overlapped, precise and detailed information can be obtained for the respective fixed positions. Consequently, the labeling at the fixed positions can be reliably captured. In particular, if a plurality of types of labeling substances are combined to change the quantity ratio so as to perform many types of labeling, an effect is demonstrated where the data analysis can be made easy or can be automated. Moreover, since the rotational movement and the straight line movement can be continually performed for measurement, an effect is demonstrated where the device and the control can be simplified, and the cost can be reduced.

A fourteenth aspect of the present invention is a continuous optical measuring method further having a light emitting position judging step for associating light received by the light receiving part with the fixed positions, based on respective intervals between the fixed positions disposed on the arrangement line, the shape and the order of the respective fixed positions, the shape of the arrangement line, or the shape of the moving line.

The fourteenth aspect of the present invention has a similar effect to that described for the second aspect of the present invention.

A fifteenth aspect of the present invention is a continuous optical measuring method having a light emission contents judging step for judging one or more wavelengths or one or more wavelength ranges included in the light received by the light receiving part, and their corresponding respective intensities.

The fifteenth aspect of the present invention has a similar effect to that described for the third aspect of the present invention.

A sixteenth aspect of the present invention is a continuous optical measuring method wherein the continuous measuring step is performed by rotation of the storage part about a predetermined axis of rotation, and elevating/lowering movement of the storage part along the axis of rotation.

The sixteenth aspect of the present invention has a similar effect to that described for the fourth aspect of the present invention.

A seventeenth aspect of the present invention is a continuous optical measuring method having: after the storing step: a reaction step for sucking a liquid suspending labeled binding substances from a fluid inlet/outlet port provided in the storage part to soak the foundation member in the liquid so as to react the binding substances and the detection substances; and a measurement preparing step for removing the binding substances and the liquid which have not contributed to the reaction.

An eighteenth aspect of the present invention is a continuous optical measuring method wherein: the storing step is for storing a foundation member into a translucent or semi-translucent storage part having a fluid inlet/outlet port at a tip end; the reaction step is for sucking the liquid or the like by using a pressure regulating part which regulates the pressure in the storage part so as to suck and discharge the fluid with respect to the storage part; the measurement preparing step is performed by discharging the liquid or the like by using the pressure regulating part; and the continuous measuring step is performed by rotating a nozzle attached with the storage part and communicated with the pressure regulating part, about its axis of rotation, or elevating/lowering it along the axial direction.

The seventeenth and eighteenth aspects of the present invention have a similar effect to that described for the ninth aspect of the present invention.

BEST MODE FOR CARRYING OUT THE INVENTION

Hereunder is a description of a continuous optical measuring apparatus and continuous optical measuring method according to an embodiment of the present invention, with reference to drawings. The description of the present embodiment should not be considered as limiting the present invention unless particularly specified.

Figure 1:
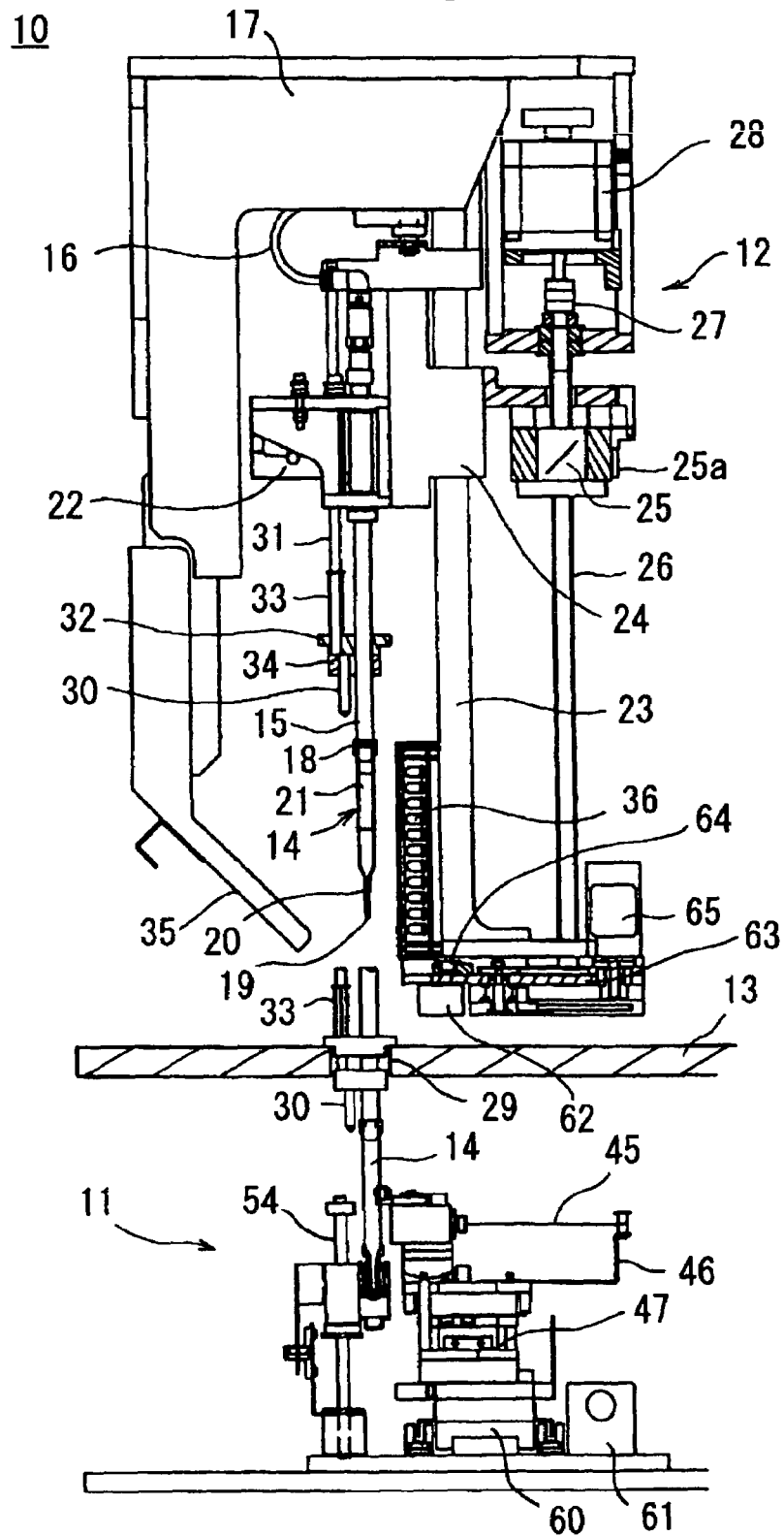
FIG. 1 is a partial cross-sectional side view of an apparatus assembled with a continuous optical measuring apparatus according to an embodiment of the present invention.

FIG. 1 is a partial cross-sectional side view of a storing, reacting and measuring apparatus 10 assembled with a continuous optical measuring apparatus 11 according to the embodiment of the present invention.

The storing, reacting and measuring apparatus 10 is an apparatus which automatically and consistently performs reaction and measurement while the abovementioned foundation member is stored in a storage part. In the storing, reacting and measuring apparatus 10, a continuous optical measuring apparatus 11 which stores the foundation member in the storage part and continually and optically measures along a line, and a storing and reacting apparatus 12 which makes the foundation member react while being stored in the storage part, are vertically provided on either side of a boundary board 13.

The storing and reacting apparatus 12 has: a plurality of (six in this example) translucent or semi-translucent pipette tips 14 serving as the storage parts having fluid inlet/outlet ports; six nozzles 15 which are attached with the pipette tips 14, rotatable about the axes thereof, and provided so as to be elevated/lowered along the axes; and a pressure regulating part 17 which are communicated with cylinders (not shown) respectively through six circular pipes 16 to regulate the pressures so as to make the six nozzles 15 suck, discharge, and store fluids with respect to the pipette tips 14.

Each pipette tip 14 has: an attachment 18 which is detachably attached to the nozzles 15; a small diameter portion 20 which has one inlet/outlet port 19 at the point and can be inserted into a container (not shown) outside of the storing and reacting apparatus 12; and a large diameter portion 21 which is provided between the small diameter portion 20 and the attachment 18, having a larger diameter than that of the small diameter portion 20 to store the foundation member.

Moreover, the pressure regulating part 17 has: six nozzles 15; a cylinder block (not shown) which has six cylinders communicated through six circular pipes 16; and a mechanism (not shown) which is connected to respective cylinder rods (pistons) (not shown) in the respective cylinder blocks so as to vertically slide the six cylinder rods all together. Furthermore, the storing and reacting apparatus 12 is provided with: a θ axis motor 22 which drives to rotate the nozzles 15, and therefore the pipette tips 14 about the axis of rotation; and a nozzle rotation mechanism which transfers the rotation to the nozzles 15 by a toothed pulley (not shown) or the like provided on the shaft of the θ axis motor 22.

Furthermore, the storing and reacting apparatus 12 has: a Z axis slider 24 on which the nozzles 15 are fixedly provided, supported by a support 23 so to be freely elevated/lowered, serving as an elevating/lowering part that allows the nozzles 15, and therefore the pipette tips 14 to be vertically elevated/lowered; a nut 25 to which the Z axis slider 24 is fixedly provided; a Z axis ball screw 26 which is screwed on the nut 25 to vertically drive the nut 25 by rotation; and a Z axis motor 28 which has a shaft connected to the Z axis ball screw 26 through a connector 27 so as to drive to rotate the Z axis ball screw 26.

By means of the elevating/lowering part, the pipette tips 14 can be lowered to the predetermined position in the continuous optical measuring apparatus 11 that is provided beneath the boundary board 13, through open holes 29 provided in the boundary board 13.

Here, the rotation mechanism part and the elevating/lowering part correspond to the nozzle rotation elevating/lowering part serving as the continuous passing/moving part.

In FIG. 1, reference symbol 25a denotes a sensor which detects any force being applied to the point of the pipette tip 14 for some reason, such as it touches with the bottom of the container.

Reference symbol 30 denotes a pin for boring a hole through a thin seal covering the opening of the container to prevent evaporation of the liquid stored in the container (not shown). The pin is vertically movable in the axial direction of the nozzle 15 by a shaft 31 linked with the piston in the cylinder. Reference symbol 32 denotes a shield which is pressed against a support plate 34 provided with the pin 30, by means of a spring 33 fixedly provided on the shaft 31. If the pipette tips 14 are lowered together with the lowering of the nozzles 15 and moved to the predetermined position beneath the open holes 29 provided in the boundary board 13, the shield 32 covers the open holes 29 to optically shield the lower side so as to make a darkroom.

Reference symbol 35 denotes a device for reflecting light from the pipette tip 14 and guiding it to a lens (the optical axis is in parallel with the axial direction of the nozzle 15) of a CCD camera (not shown) provided above, so as to monitor the operation of the pipette tip 14. Moreover, reference symbol 36 is a back light for irradiating light to the pipette tips 14.

Furthermore, reference symbol 60 denotes a nozzle disposition direction movement guiding part 60 serving as a nozzle disposition direction moving part for moving the light receiving part 40 in the disposition direction of the nozzles. Reference symbol 61 denotes a motor and a ball screw for moving the nozzle disposition direction movement guiding part 60 in the front and back direction of the drawing. Furthermore, reference symbol 62 denotes a magnet for applying a magnetic force to the inside of the pipette tips 14. Reference symbol 63 denotes a plate to which the magnet 62 is attached, and provided so as to be made closer to and separated from the pipette tips 14. When the plate 63 becomes closer to the pipette tips 14, the magnetic force is applied to the inside of the pipette tips 14. When it is separated, the magnetic force is not applied to the inside of the pipette tips 14. A fluid drip receiving part 64 for receiving fluid dripping from the pipette tips 14 is provided on the plate 63. Reference symbol 65 denotes a motor 65 for moving the plate 63. Using this structure, by applying or not applying the magnetic force to the inside of the pipette tips 14, magnetic particles passing through or stored in the pipette tips 14 can be separated. As a result, various processes can be performed consistently with only this apparatus, so that the process efficiency is high. Details of the continuous optical measuring apparatus 11 in the FIG. 1 are described later.

Figure 2:
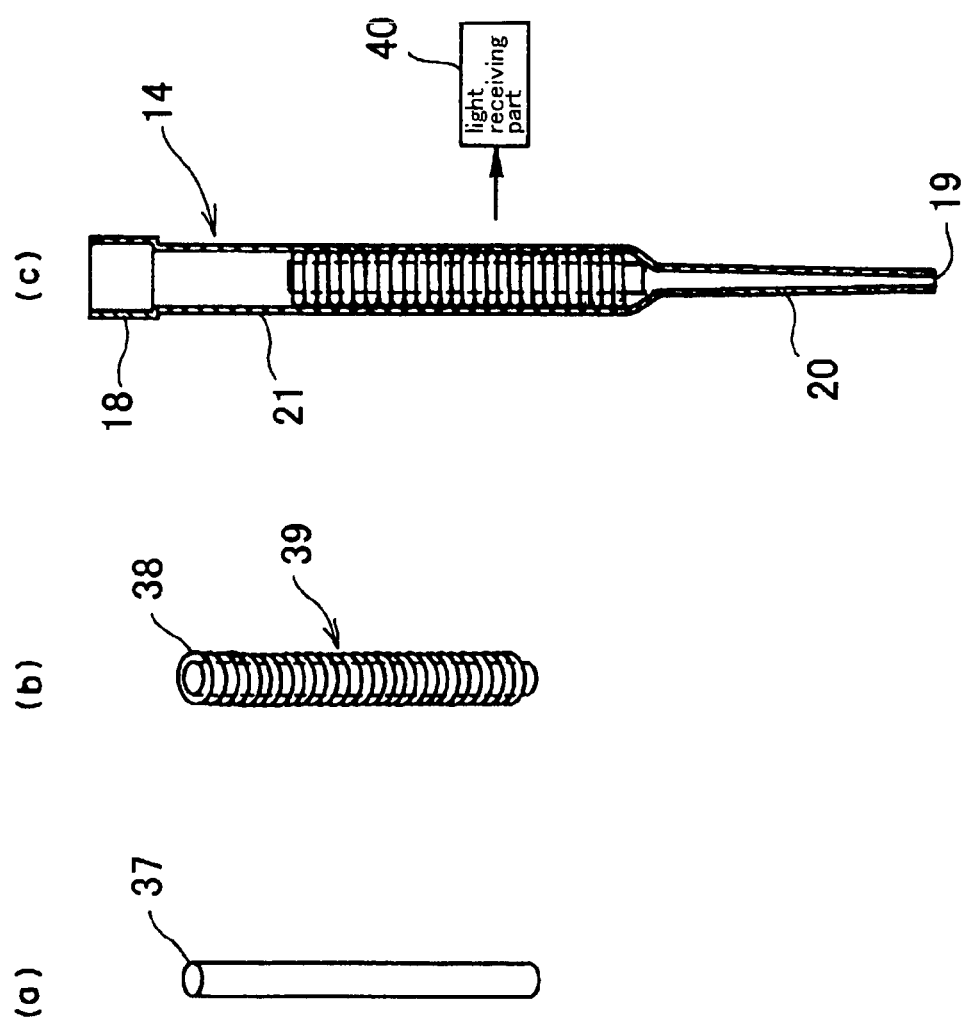
FIG. 2 shows a foundation member according to the embodiment of the present invention, and a state with the foundation member stored.

FIG. 2 shows a foundation member to be stored in the pipette tip 14 serving as the storage part, and a state with the foundation member stored therein.

FIG. 2 (a) shows a core 37 serving as a rod-shaped or cylindrical support for supporting the foundation member 38 by wrapping it around the surface thereof. FIG. 2 (b) shows an integrated support 39 wrapped with the foundation member 38. Here, the diameter of the core 37 is for example, about 2 to 4 mm, the thickness of the foundation member 38 is for example, about 0.05 mm to 0.2 mm, and the length of the foundation member 38 is for example, about 500 mm to 3000 mm. FIG. 2 (c) shows the state where the integrated support 39 is stored in the pipette tip 14. The line along the longitudinal direction of the foundation member 38 corresponds to the arrangement line, and the diameter of the foundation member 38 approximately corresponds to the width of the arrangement line.

Figure 3:
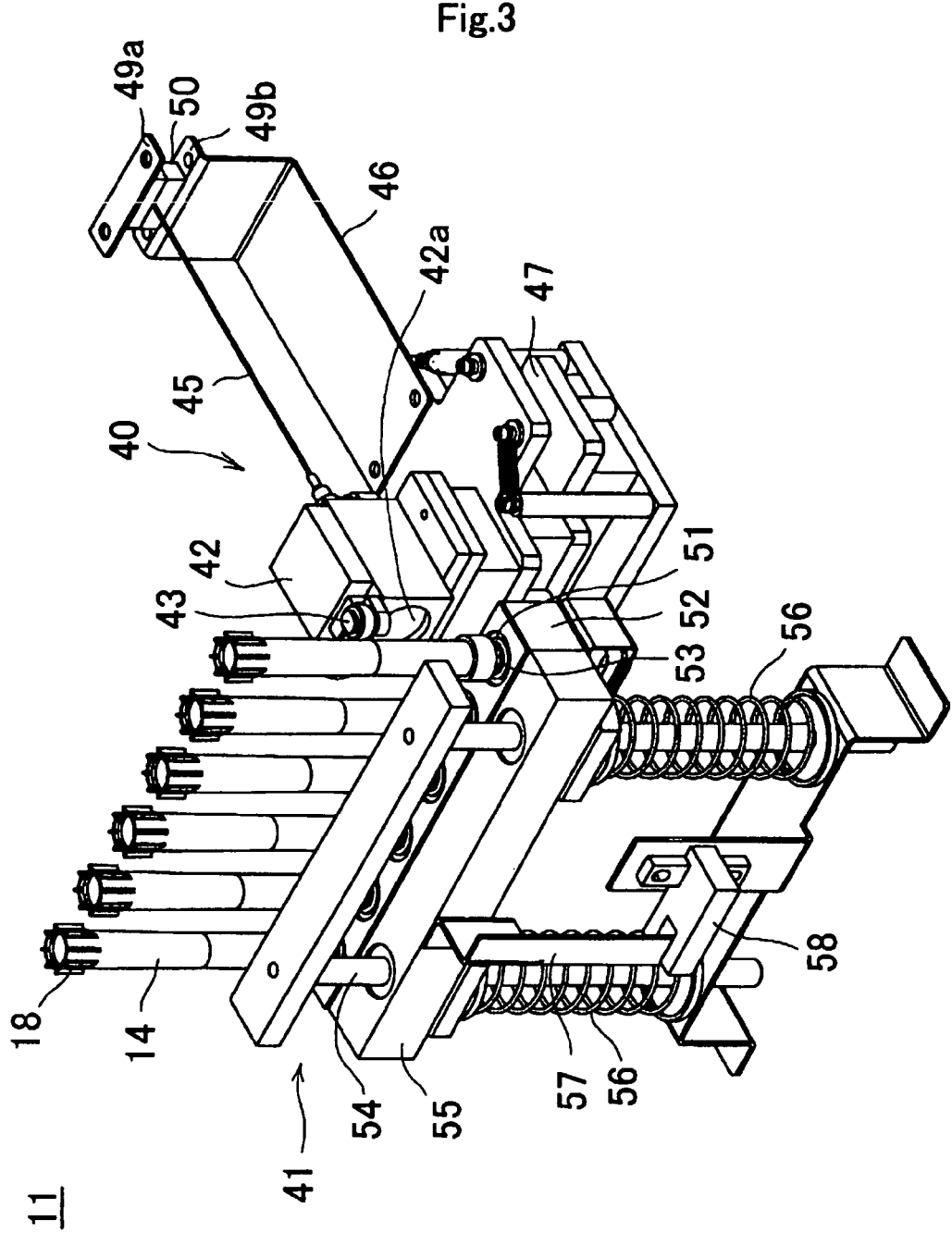
FIG. 3 is a perspective view of the main part of the continuous optical measuring apparatus according to the embodiment of the present invention.
Figure 4:
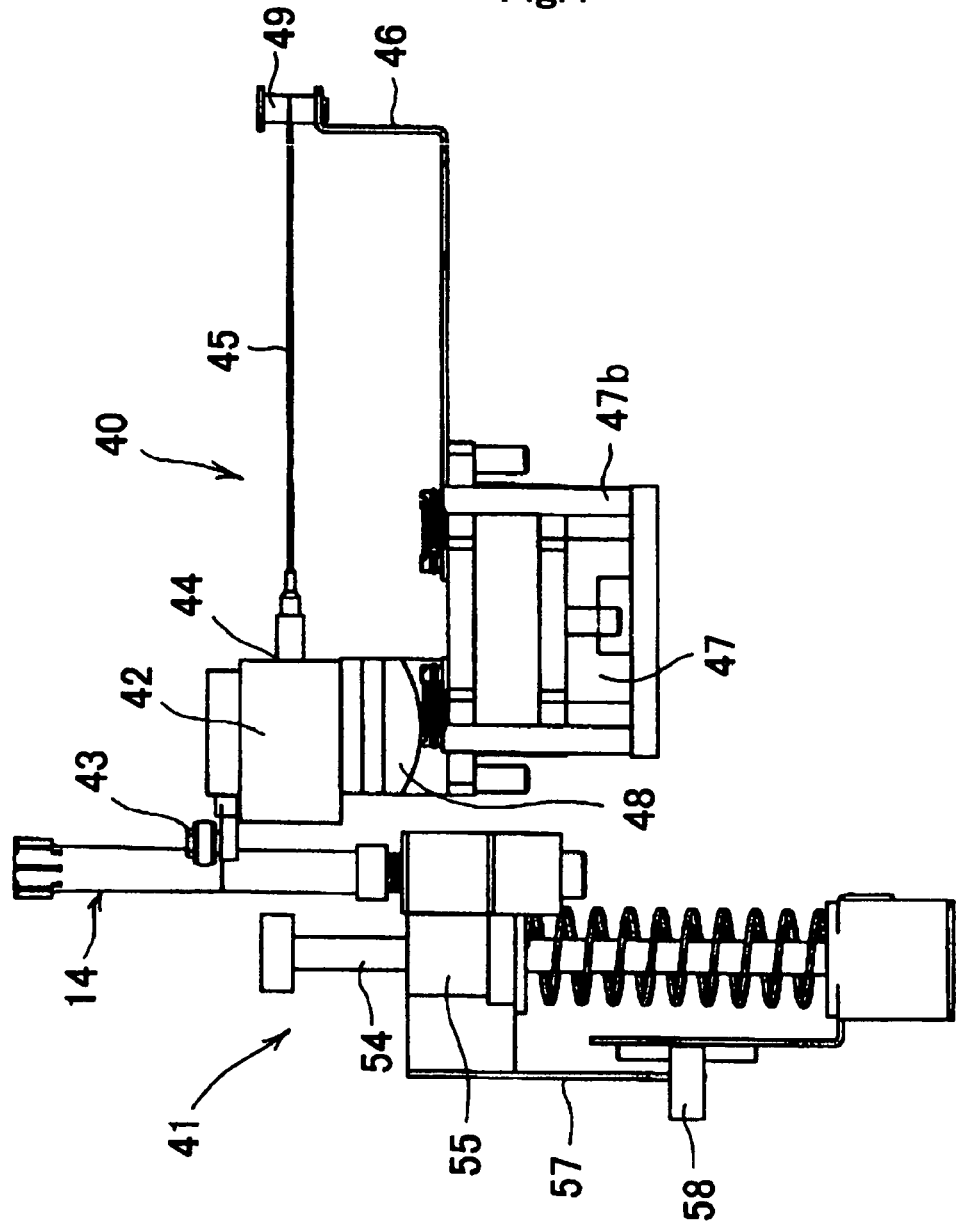
FIG. 4 is a side view of the main part of the continuous optical measuring apparatus according to the embodiment of the present invention.
Figure 5:
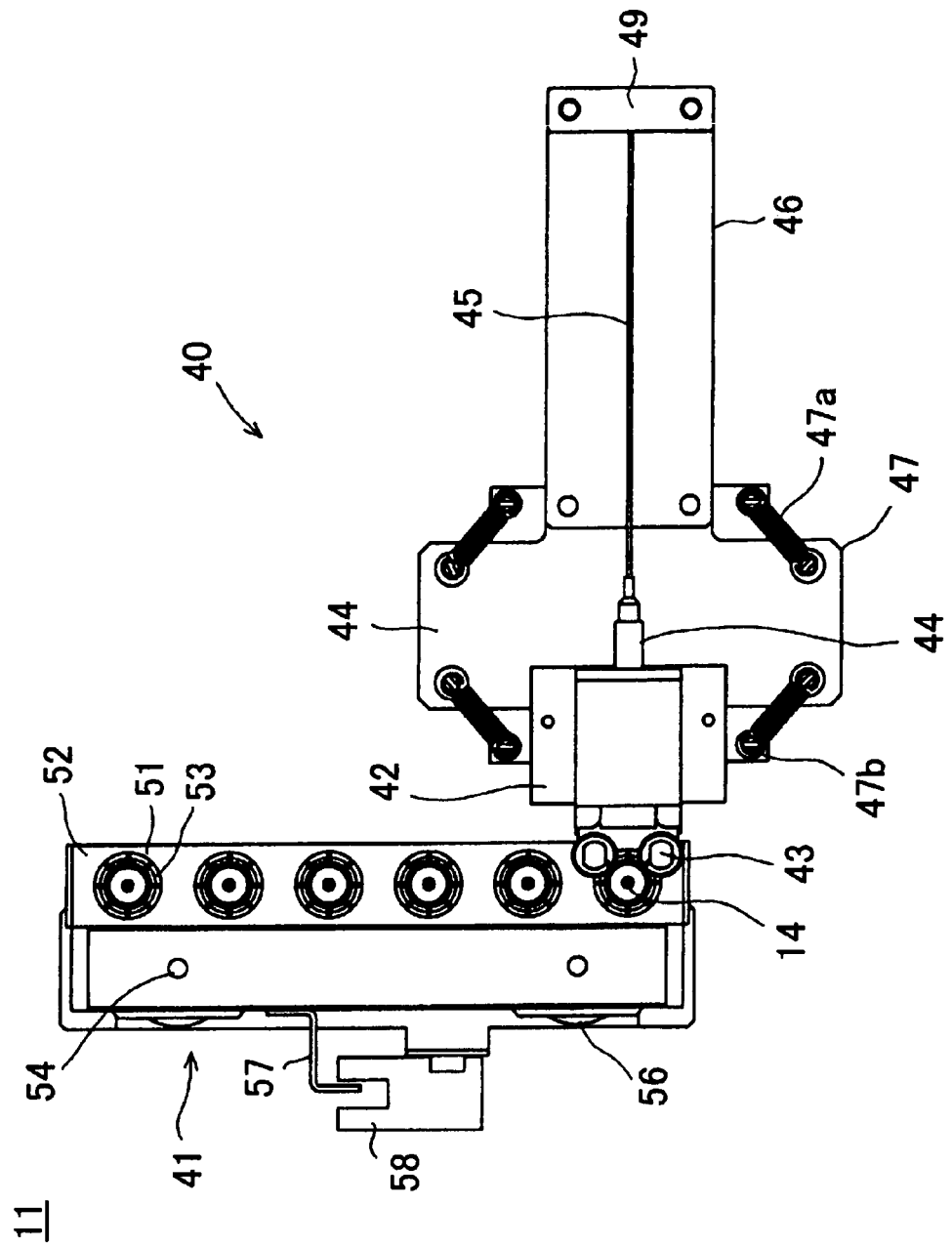
FIG. 5 is a plan view of the main part of the continuous optical measuring apparatus according to the embodiment of the present invention.

Next is a description of the continuous optical measuring apparatus 11 according to the present embodiment, with reference to FIG. 3, FIG. 4, and FIG. 5.

The continuous optical measuring apparatus 11 has: a light receiving part 40 which is provided in a predetermined position outside of the pipette tips 14, and capable of receiving light from the pipette tips 14; the aforementioned nozzle rotation elevating/lowering part which is provided on the storing and reacting apparatus 12, and moves the pipette tips 14 relatively with respect to the light receiving part 40 so as to scan all fixed positions of the foundation member 38, along a moving line different from the arrangement line having a predetermined line width along the longitudinal direction of the foundation member 38; and a guide part 41 which holds the pipette tips 14 in a position where the light receiving part 40 can receive the light from the pipette tips 14.

The light receiving part 40 has: a light receiving head 42 which has an optical system wherein the focal distance is adjusted so as to be capable of receiving light having a predetermined light receiving width from the respective fixed positions on the foundation member stored in one of the pipette tips 14; and a positioning roller 43 which is in contact with the pipette tips 14, for maintaining a fixed distance from the end surface of the light receiving head 42 to the one pipette tip 14. The optical system installed in the light receiving head 42 has, for example a light receiving width of approximately 0.02 mm on the foundation member.

Moreover, the light receiving part 40 has: an optical fiber 45 of which a point 44 is attached to the light receiving head 42; a support frame 46 which supports the optical fiber 45; an XY axis direct-acting part 47 which holds the light receiving head 42 and the support frame 46 so as to be movable in the horizontal direction for a minute distance. The XY axis direct-acting part is formed by overlapping an X axis direct-acting part and a Y axis direct-acting part, and is movably supported on fixed columns 47b by springs 47a. Furthermore, the light receiving head 42 is mounted on a gonio stage 48 so that the angle of the light receiving head 42 becomes adjustable in a vertical plane. Using these devices, in the optical system of the light receiving head 42, the distance, the position, and the angle with respect to the one pipette tip 14 can be minutely adjusted so as to adjust to the best focal distance for the optical system. The optical fiber 45 is attached to the support frame 46 by a fiber pressing sponge 50 clamped between optical fiber holding metal fittings 49a and 49b. Reference symbol 42a denotes an opening for introducing light to the optical system provided in the light receiving head 42.

Next, the guide part 41 has a guide block 52 provided with six retention holes 51 which rotatably hold the lower part of the six pipette tips 14. A spring 53 that urges the pipette tip 14 upward is provided for each retention hole 51, so as to absorb the downward force applied to the pipette tip 14 to some degree.

The guide block 52 is attached to a slider 55 that is provided movably in the vertical direction along two shafts 54. The slider 55 is urged upward by two compression springs 56 provided around the respective shafts 54, so that the pipette tips 14 inserted into the guide block 52 are positioned relative to the predetermined position provided with the light receiving head 42 of the light receiving part 40. In that case, the slider 55 is provided with a photo micro sensor 58 attached by a sensor bent plate 57. The photo micro sensor 58 is provided with a light emission element and a photodetector, and up until the sensor bent plate 57 blocks between these, the pipette tips 14 are pressed down by the nozzle elevating/lowering part. As a result, the pipette tips 14 are positioned at a position that is measurable by the light receiving head 42.

As described above, the whole light receiving part 40 can be moved along the disposition direction of the six pipette tips 14 which have been positioned in the guide part 41 by the nozzle disposition direction movement guiding part 60 serving as the nozzle disposition direction moving part. As a result, it can be serially moved to each of the six pipette tips 14, and the measurement can be performed one by one.

In the present embodiment, additionally there are an information processor in which is stored a CPU, a memory device, and various programs, input devices such as a keyboard, a mouse, and the like, and output devices such as a display panel, a printer, and the like (not shown). The light emitting position judging part, the light emission contents judging part, and the control unit which gives operation instructions to the storing and reacting apparatus and the continuous optical measuring apparatus, are constituted by the information processor.

Next is a description of the operation of the continuous optical measuring apparatus 11 according to the present embodiment.

The integrated supports 39 having the foundation member 38 wrapped around the core 37 are respectively stored in the six pipette tips 14. A large number of the fixed positions are formed on the foundation member at predetermined intervals. The respective fixed positions are fixed with for example, oligonucleotides having respective predetermined base sequences, as the detection substances. The six pipette tips 14 are attached to the six nozzles 15 in the storing and reacting apparatus 12. Then, by the nozzle disposition direction movement guiding part 60 of the nozzle disposition direction moving part, the light receiving part 40 is moved to the first container out of the six container positions which store; liquids suspended with six types of target substances, for example that are binding substances labeled with a plurality of types of fluorescent substances and used to examine structures, and other necessary reagents.

When the reaction is completed, the residual liquid is discharged and a measuring liquid such as distilled water is newly sucked, and the storing and reacting apparatus 12 is positioned above the boundary board 13 so that the open holes 29 come directly under the pipette tips 14. In this state, by the nozzle elevating/lowering part, the lower parts of the six pipette tips 14 are inserted through the open holes 29 into the respective retention holes 51 provided in the guide block 52 of the guide part 41 in the continuous optical measuring apparatus 11, and the points thereof are pressed down. In that case, upward force is applied to the pipette tips 14 by the springs 53 provided in the retention holes 51 and the compression springs 56. The vertical positioning is performed by the photo micro sensor 58. In this case, since the open holes 29 in the boundary board 13 are covered by the shield 32, the surroundings of the continuous optical measuring apparatus 11 are shielded from light from the storing and reacting apparatus 12, and a darkroom is made.

Since the pipette tips 14 are in contact with the positioning roller 43, the distance from the end surface of the light receiving head 42 is maintained at a fixed level.

In this state, by the nozzle rotation elevating/lowering part, the pipette tips 14 are moved by the combination of rotation operation and elevation operation while the adjacent spirals are in contact, or overlapped with each other, with the line width, that is the light receiving width of 0.02 mm in this example, which is different from the width of about 0.08 mm in this example, along the longitudinal direction of the foundation member 38, that is the arrangement line, as the spiral light receiving line. For example, if the height is 20 mm in the case where the foundation members 38 are wrapped on the cores 37 while the foundation members 38 are in contact with each other, when the rotation and elevation movement is performed along the moving line such that the adjacent spirals with the light receiving width of 0.02 mm are in contact with each other, then the pipette tips 14 are rotated for 20/0.02, that is 1000 times. Moreover, if the rotation and elevation movement is performed along the moving line such that the light receiving width is overlapped by 0.01 mm, then the pipette tips 14 are rotated for 20/0.01, that is 2000 times In consequence, light from the respective fixed positions disposed on the foundation member 38 is serially transmitted to the optical fiber 45 through the lens system of the light receiving head 42.

Once the measurement of the first pipette tip 14 is completed, the nozzle disposition direction movement guiding part 60 is moved to move the light receiving part 40 to the second nozzle position, and the next measurement is performed. In this manner, all of the six pipette tips 14 can be measured.

In the above example, since the light emission from the respective fixed positions is measured along the moving line which is finer than the arrangement line, the light emission from the same fixed position is repeatedly captured for a plurality of times. As a result, since the light emission from the different parts can be captured even in the same fixed position, the fixed positions can be measured in more detail.

The optical fiber 45 is provided with filters which branch light into a plurality of transmission paths and allow only a plurality of respective wavelengths from the fluorescent substances to pass respectively, and photometers which measure the intensity of light passing through the respective filters. The device corresponds to the light emission contents judging part.

As a result, the light emitting position judging part constituted by programs in the information processor (not shown) associates the respective light emitting positions with the fixed positions based on; the intervals between the fixed positions disposed on the arrangement line, the order of the respective fixed positions on the arrangement line, the width, the moving line, or the light receiving width. Then, by combining these with the judged results of the light emission contents judging part, the base sequences or the affinity of the target substances are judged.

The respective embodiments described above are specific explanations for better understanding of the present invention, and are not to be considered as limiting other embodiments. Consequently, modifications can be made without departing from the scope of the present invention. For example, in the above embodiment, the nozzle rotation elevating/lowering part in the storing and reacting apparatus has been used as the continuous passing/moving part. However, the present invention is not limited to this case, and for example a device which rotates and elevates the storage part may be provided separately and independently from the storing and reacting apparatus.

Moreover, the present invention is not limited to the case where an oligonucleotide is used as the detecting substance. For example, it may use not only an other genetic substance but also an immunity substance, an amino acid, a protein, a sugar, and the like. Moreover, the first embodiment is described regarding the case where a pump is used as the sucking and discharging part, however the present invention is not limited to this case, and for example it may be constituted by a cylinder and a cylinder rod (piston).

As the measuring device, the device may not only measure the fluorescence, but may also measure chemical light emission or electromagnetic waves having various wavelengths. For example, as the electromagnetic waves, the wavelength range of electromagnetic waves of infrared rays, ultraviolet rays, X rays, electric waves, and the like besides the visible light may be measured.

Furthermore, in the above description, the description is regarding the case where the respective pipette tips are six. However, the present invention is not limited to this case, and the case may be such that an other number of pipette tips, or slender pipes are provided together. The numerical values used in the above description are exemplary and are not to be considered as limiting. The respective components constituting the continuous optical measuring apparatus and the storing and reacting apparatus described in the respective embodiments may be optionally selected and combined while adding appropriate modifications.

If the measurement is performed by rotating the storage part, then as a measurement positioning part for preventing rotational displacement, the vicinity of the measurement position may be provided with, for example a guide member which is in contact with the peripheral surface of the storage part (pipette tip), for example the peripheral surface of the large diameter portion or the small diameter portion, at one point, or which contacts so as to hold between a plurality of points, or which is in contact around the whole periphery, so as to guide the rotation. Alternatively, there may be provided a mechanism which drives to rotate the storage part in combination with the storage part itself.

In the abovementioned process, the description is regarding the case where the arrangement line is along the slender foundation member. However, the arrangement line can be applied even if it is not along the slender foundation member.

The invention claimed is:

1. A continuous optical measuring apparatus comprising:
at least one transparent or semi-translucent storage part capable of storing a foundation member having a plurality of types of predetermined detection substances fixed thereto along an arrangement line at predetermined intervals, with the detection substances and their fixed positions associated;
at least one light receiving part installed at a predetermined position outside of said storage part, and receiving light from said fixed positions, and receiving light from an area having a light receiving width narrower than the width of said arrangement line; and
a continuous moving part which is continuously moved relatively between said light receiving part and said storage part so as to scan said fixed positions on said foundation member along a spiral moving line having said light receiving width,
wherein said continuous moving part has a rotation and straight line moving part which can rotate said storage part about a predetermined axis of rotation, and linearly move said storage part along said axis of rotation.

2. A continuous optical measuring apparatus according to claim 1, having a light emitting position judging part which associates light received by said light receiving part with said fixed positions, based on respective intervals between the fixed positions disposed on said arrangement line, the shape and the order of the respective fixed positions, the shape of said arrangement line, or the shape of said moving line.

3. A continuous optical measuring apparatus according to either one of claim 1 and claim 2, having a light emission contents judging part which judges one or more wavelengths or one or more wavelength ranges included in the light received by said light receiving part, and/or their corresponding respective intensities.

4. A continuous optical measuring apparatus according to any one of claim 1 and claim 2, wherein said foundation member is a foundation member in a slender shape such as a thread, a cord, or a tape having the respective fixed positions arranged along the longitudinal direction, and the foundation member is wrapped, laminated or aligned, and integrated in a condition where the respective fixed positions are measurable from the outside.

5. A continuous optical measuring apparatus according to any one of claim 1 and claim 2, wherein said foundation member itself or the integrated foundation member, and said storage part are rotation bodies, and are stored so that their central axes coincide.

6. A continuous optical measuring apparatus according to any one of claim 1 and claim 2, wherein said light receiving part is provided with an optical system which enables focusing on the respective fixed positions of said foundation member stored in said storage part.

7. A continuous optical measuring apparatus according to any one of claim 1 and claim 2, wherein said light receiving part is attached with a point of one optical fiber.

8. A continuous optical measuring apparatus according to any one of claim 1 and claim 2, wherein said storage part has a fluid inlet/outlet port, and is detachably attached to a nozzle which communicates with a pressure regulating part which regulates the pressure in said storage part so as to suck and discharge the fluid with respect to said storage part, and said continuous moving part is a nozzle rotation elevating/lowering part that rotates said nozzle about said axis of rotation and elevates/lowers it along the axial direction.

9. A continuous optical measuring apparatus according to claim 3, having a holding part which rotatably holds a lower part of said storage part so that said storage part can be positioned at a position allowing said light receiving part to receive light.

10. A continuous optical measuring apparatus according to any one of claim 1 and claim 2, wherein said light receiving part is supported so that minute movements can be made so as to keep the distance from the storage part constant, in accordance with fluctuations accompanying the rotational movement of said storage part.

11. A continuous optical measuring apparatus according to any one of claim 1 and claim 2, wherein said optical fiber can irradiate predetermined light through said optical fiber, and can receive light through said optical fiber.

12. A continuous optical measuring method comprising:
a storing step for storing into at least one transparent or semi-translucent storage part a foundation member having a plurality of types of predetermined detection substances fixed thereto along an arrangement line at predetermined intervals, with the detection substances and their fixed positions associated;
a moving step for moving so as to position at least one light receiving part which receives light from an area having a light receiving width narrower than the width of said arrangement line, from said storage part, to a predetermined position outside of the storage part; and a continuous measuring step for measuring while continuously moving relatively between said light receiving part and said storage part so as to scan said fixed positions on said foundation member along a spiral moving line having said light receiving width, wherein said continuous measuring step is performed by rotation of said storage part about a predetermined axis of rotation, and elevating/lowering movement of said storage part along said axis of rotation.

13. A continuous optical measuring method according to claim 12, further having a light emitting position judging step for associating light received by said light receiving part with said fixed positions, based on respective intervals between the fixed positions disposed on said arrangement line, the shape and the order of the respective fixed positions, the shape of said arrangement line, or the shape of said moving line.

14. A continuous optical measuring method according to either one of claim 12 and claim 13, having a light emission contents judging step for judging one or more wavelengths or one or more wavelength ranges included in the light received by said light receiving part, and their corresponding respective intensities.

15. A continuous optical measuring method according to any one of claim 12 and claim 13, having: after said storing step:

a reaction step for sucking a liquid suspending labeled binding substances from a fluid inlet/outlet port provided in said storage part to soak said foundation member in the liquid so as to react said binding substances and said detection substances; and a measurement preparing step for removing said binding substances and said liquid which have not contributed to the reaction.

16. A continuous optical measuring method according to any one of claim 12 and claim 13, wherein: said storing step is for storing a foundation member into a translucent or semi-translucent storage part having a fluid inlet/outlet port at a tip end; said reaction step is for sucking said liquid or the like by using a pressure regulating part which regulates the pressure in said storage part so as to suck and discharge the fluid with respect to said storage part; said measurement preparing step is performed by discharging said liquid or the like by using said pressure regulating part; and said continuous measuring step is performed by rotating a nozzle attached with said storage part and communicated with said pressure regulating part, about its axis of rotation, and elevating/lowering it along the axial direction.

* * * * *